United States Patent [19]

Durand et al.

[11] Patent Number: 5,670,437
[45] Date of Patent: Sep. 23, 1997

[54] METHOD OF PREPARATION OF A HYDROGENATION CATALYST SOLUBLE IN AN ORGANIC LIQUID PHASE

[75] Inventors: Daniel Durand, Rueil Malmaison; Gérard Hillion, Herblay; Patrick Sarrazin, Rueil Malmaison, all of France

[73] Assignee: Institut Francais du Petrole, Rueil-Malmaison, France

[21] Appl. No.: 372,396

[22] Filed: Jan. 13, 1995

[30] Foreign Application Priority Data

Jan. 13, 1994 [FR] France .................. 94 00413

[51] Int. Cl.$^6$ .................. B01J 31/00; B01J 37/00; C08F 4/02; C08F 4/60
[52] U.S. Cl. .................. 502/104; 502/103; 502/113; 502/117; 502/111; 585/250; 585/270; 585/275; 585/277
[58] Field of Search .................. 502/113, 117, 502/104, 111; 585/250, 270, 275–277, 379

[56] References Cited

U.S. PATENT DOCUMENTS

| | | | |
|---|---|---|---|
| 3,541,064 | 11/1970 | Yoshimoto et al. | 585/250 |
| 4,062,804 | 12/1977 | Ueno et al. | 502/104 |
| 4,258,226 | 3/1981 | Dozzi et al. | 585/270 |
| 4,271,323 | 6/1981 | Durand et al. | 585/277 |
| 4,357,478 | 11/1982 | Hillion et al. | 585/250 |
| 4,581,417 | 4/1986 | Buding et al. | 525/338 |
| 4,631,315 | 12/1986 | Buding et al. | 525/338 |
| 4,980,331 | 12/1990 | Hoximeier et al. | 502/117 |
| 5,547,675 | 8/1996 | Canich | 502/117 |

FOREIGN PATENT DOCUMENTS

| | | |
|---|---|---|
| 0008304 | 2/1980 | European Pat. Off. . |
| 0368419 | 5/1990 | European Pat. Off. . |
| 0488073 | 6/1992 | European Pat. Off. . |
| 0531174 | 3/1993 | European Pat. Off. . |

*Primary Examiner*—Glenn A. Caldarola
*Assistant Examiner*—J. Pasterczyk
*Attorney, Agent, or Firm*—Millen, White, Zelano, & Branigan, P.C.

[57] ABSTRACT

The method of preparation comprises:

a step (a) of placing in solution at least one compound of at least one metal A in at least one organic solvent S, and of at least one reducing compound R of at least one metal B in at least one organic solvent S', a step (b) of placing the reducing compound R in contact with the metal A compound, a step (d) of neutralisation of the residual reducing functions of the reducing compound R with at least one oxidizing agent O, and where applicable the addition of a selectivity agent P either during step (a) or during step (c) placed between steps (b) and (d), The catalyst obtained can be used in selective or total hydrogenation.

35 Claims, No Drawings

METHOD OF PREPARATION OF A HYDROGENATION CATALYST SOLUBLE IN AN ORGANIC LIQUID PHASE

BACKGROUND OF THE INVENTION

The present invention concerns a method for production of hydrogenation catalysts in a homogeneous phase, soluble in organic media, where applicable saturated with water dissolved in the reaction medium (discrete water). It also concerns catalysts obtained by this method, and the hydrogenation method.

These catalysts can be used, for example in selective or total hydrogenation of unsaturated mono-olefinic or polyolefinic, acetylenic or aromatic compounds and of saturated or unsaturated functional compounds such as alcohols, aldehydes, organic acids, ketones, phenols, esters, nitriles, sulfones, imines, amines and nitrated derivatives.

Catalysts soluble in the reaction medium which are prepared from precious metal complexes are known from U.S. Pat. Nos. 4,581,417 and 4,631,315.

Other soluble catalysts can be prepared from non-precious metals and in particular from transition metals such as iron, cobalt and nickel.

In order for the catalysts to be active during hydrogenation and soluble in the organic medium, they have to be prepared by the placing in contact of a salt of said metals, and more particularly of a carboxylate, with a reducing compound of the alkylalluminium type as in U.S. Pat. No. 4,357,478 or otherwise with an organic compound of lithium or magnesium as in U.S. Pat. No. 3,541,064.

U.S. Pat. No. 4,271,323 also describes a method of hydrogenation with a heptane soluble catalyst obtained by reaction of a reducing organometallic lithium, sodium and/ or aluminium compound with a mixture on the one hand of a (generally carboxylate) nickel compound or cobalt, and on the other hand a zinc, iron or zirconium, manganese or molybdenum compound.

Reducing compounds such as sodium hydride or mixed sodium and aluminium hydride can also be used as in U.S. Pat. No. 4,258,226.

Nickel or cobalt compounds together with alkylalumoxanes as the reducing agent can be used in order to selectively hydrogenate copolymers of conjugated dialkenes and of unsaturated aromatic alkyls, as in U.S. Pat. Nos. 4,980,331 and 5,030,779.

All of these compounds are active, in various degrees, in the hydrogenation of unsaturated aromatics or hydrocarbons. Nevertheless, in the presence of discrete water (water dissolved in the reaction medium) a progressive agglomeration of the (insoluble) catalyst with, as a corollary, a progressive reduction in catalytic activity is observed, and in the case of selective hydrogenation of polyolefins or of alkynes, an increase in the selectivity of the reaction towards the formation of undesirable saturated products.

SUMMARY OF THE INVENTION

A new technique has now been discovered for keeping the catalyst in a perfect condition of solubility in the reaction medium. This technique involves neutralizing all the reductive functions of the reducing agent which would not have reacted with the reducible metal salts. This neutralization is generally implemented by the introduction of an oxidizing agent after the formation of the active catalytic component. It thus generally takes place before storage of the catalyst or before introduction thereof into the reaction medium.

By improving the solubility of the catalyst in the presence of water, the invention allows the activity and selectivity of the catalyst to be increased. It allows, on the one hand, prevention of the formation of unwanted deposits of catalyst which has been rendered practically inactive by agglomeration on the walls of the reactor and the exchangers, and on the other hand the use of weaker concentrations of metals, which is also advantageous as the removal of metals from a homogeneous liquid hydrogenate is always complex.

An object of the invention is thus a method of preparation of a catalyst particularly useable for hydrogenation in a homogeneous phase, said catalyst being soluble in an organic medium, comprising:

a step (a) of placing in solution on the one hand at least one compound of at least one metal A in at least one organic solvent S, and on the other hand of at least one reducing compound R of at least one metal B in at least one organic solvent S', a step (b) of placing the reducing compound R in contact with the metal A compound, a step (d) of neutralization of the residual reducing functions of the reducing compound R with at least one oxidizing agent O.

The method can advantageously comprise the addition of a selectivity agent P to the solution of meted A compound obtained in step (a) before reduction thereof by the reducing compound R of metal B, and/or preferably the addition takes place in a step (c) in the product resulting from step (b).

Step (b) of reduction of metal (A), step (c) of selecting the catalyst by the agent (P) and step (d) of neutralizing with compound (O) are preferably followed by a ripening step at a temperature of between −20° C. and 200° C. (or preferably 150° C.) for between 0.1 min. and 100 hrs, preferably 10 min. and 75 hrs, and most advantageously between 10 mins. and 50 hrs.

The aim of the ripening is to obtain stabilized intermediate preparations before going on to the next step in preparation.

The solutions of metal A compound and reducing compound R can be produced with the same solvent or with two different solvents. Nevertheless, to ensure purity of the products, it is preferable to use the same solvent and if possible for this solvent to be either the product to be hydrogenated or the product resulting from the hydrogenation.

The solvents S and S' allow the solubility of both the metal A compounds and the metal B reducers. The solvents are saturated or unsaturated hydrocarbons, monoaromatic compounds (benzene, toluene, xylenes). saturated or unsaturated alkylbenzenes, polyaromatics (naphthalene), saturated or unsaturated monocyclic or polycyclic compounds (cyclohexane, cyclohexene, decalin™ and tetralin™), oxides, ethers tetrahydrofuran of oxide ethers (methylic ethers or diethylene glycol).

These solvents have to be exempt from traces of oxidizing agents such as water, alcohols and oxygen, as the presence of these agents has the disadvantage of initially destroying a part of the reducing function of the reducing agent and of handicapping its activity with respect to the reduction of the metal A compound. The solvents are preferably de-aerated and saturated in inert or reducing gas (nitrogen, argon, hydrogen).

The metal A is selected from one of the metals of groups Ib, IIb, Vb, VIb, VIIb and VIII and preferably Ib, VIb, VIIb and VIII of the periodic classification, and more particularly iron, cobalt and nickel, chromium molybdenum, manganese and zinc.

These metals can be introduced in the form of halides, sulphides, or acetylacetonates, but preferably in the form of inorganic acid carboxylates, having 2 to 25 carbon atoms. Among the latter, mention may be made of acetates, octoates, decanoates, naphthanates, stearates, palmitates, oleates and benzoates.

The concentrations of these metal A compounds in the solvent S, and prior to being placed in contact with the reducing compound R, are between 0.01 and 10 moles per liter and preferably between 0.05 and 5 moles per liter.

The metal B reducing compounds R are organometallic derivatives of at least one metal B selected from the group formed by lithium, sodium, aluminium and more particularly of mixed derivatives of aluminium and sodium and/or lithium. They have at least one carbon-metal or hydrogen-metal bond. Each of said bonds corresponds to a reducing function.

Among said reducing compounds R, mention may be made of triethylaluminium, triisobutylaluminium, chlorodiethylaluminium, diethylbutoxyaluminium, diethoxyethylaluminium, diisobutylaluminium hydride, mixed lithium and aluminium hydride, mixed sodium and aluminium hydride, mixed sodium and boron hydride, butyllithium, sodium ethylate and their derivatives by substitution either by a hydrocarbonic radical or an alkoxy group. The maximum degree of substitution in these substitution derivatives is equal to the sum of carbon-metal and/or hydrogen-metal bonds minus one, which will permit the reduction of the metal A.

The solutions of these reducing compounds have, as above, to be prepared in the absence of oxidizing compounds, and in particular in the absence of air, water, alcohols etc. The concentration of reducing compound R is between 0.01 and 10 moles per liter, and preferably between 0.05 and 5 moles per liter.

The second step (b) consists of partially or totally reducing the metal A compound by means of the metal B reducing compound R in a state of oxidation for which it is most active for the reaction considered. The placing in contact of these two reactants, still in the absence of other oxidizing compounds takes place in a neutral atmosphere (for example in argon or nitrogen) or reducing atmosphere (for example in hydrogen) either by the introduction of the A metallic compound to the reducing compound R, or inversely, or else either by simultaneous introduction of the 2 reactants in a mixing line or in a preparation reactor in the absence of other oxidizing products. In all these cases, it is desirable for the medium to be agitated to encourage a homogeneous reduction of the metal A compound by means of the reducing agent R.

In order for fie reduction of metal A to lead to the most active catalytic component, it is desirable for the ratio between the number of reducing functions (carbon-metal and/or metal-hydrogen bond of compound R) and the sum of the degrees of oxidation of the metals A (between their state of oxidation in the compound used and zero degrees) is between 0.1 and 20 and in a preferred manner, between 0.5 and 10.

The temperature for contacting the metal A compound with the metal B reducing compound is between −20° C. and +200° C., and preferably between 0° and 150° C.

This step of reducing the metal A is preferably carried out in a neutral or reducing atmosphere. This reaction medium can be produced by the introduction of hydrogen at partial pressures between 0 and 200 bar, preferably between 0.01 and 50 bar, and most advantageously between 0.1 and 10 bar.

A ripening step in a neutral or reducing atmosphere allows the operating conditions to be adjusted so that the amount of reduction of the metal A by the reducer is optimum.

The addition of selecting agent is to introduce one or more metallic or organic elements P into the catalytic composition and more particularly into the product resulting from the reduction of the metal A compound by the metal B reducing agent R, allowing more selectivity for selective hydrogenation of alkyne or polyolenic or polyfunctional type compounds in mono-olefinic, or monofunctional, etc. products to be conferred upon the finished catalyst.

Among the metallic elements which can carry out this role, mention can be made of the metals in groups IA and IIA and IIB of the periodic classification, as well as elements such as yttrium, titanium, zirconium, gallium, gerranium, arsenic, tin and lead, phosphorous and antimony.

The compounds providing increased selectivity can be selected from among the phosphine, phosphite and amine families, sulphurareal compounds such as thiophene, dimethyl sulphide and nitrogenous compounds such as pyridine and piperdine.

The atomic or molar ratio (according to the nature of the agent P) between the selecting agent P and the metal A is between 0.001 and 10 and preferably between 0.01 and 5.

As in the reduction step, selectivity step (c) is carded out in a neutral or reducing gas atmosphere, advantageously at the same partial pressures, and is followed by a ripening step.

The selecting agent P can also be Introduced into the metal A compound solution before step (b) of reduction by means of the metal B reducing compound. This solution is generally adopted when the selecting agent is a metallic compound.

Step (d) of neutralizing the residual reducing functions of the reducing agent R still present after reduction of metal A and where applicable reaction with the selectivity agent P, consists of introducing an oxidizing agent O which allows the excess reducing compound R to be oxidized while retaining the whole of the catalytic preparation which is soluble even in an organic medium, saturated in discrete water.

These oxidizing agents O are preferably selected from the primary or secondary long-chain aliphatic alcohol families (the number of carbon atoms being equal to or more than 6) such as hexanol, decanol or dodecanol, methylheptanols or ethylhexanols, linear or branched tertiary alcohols such as tertbutanol or 2,3-dimethyl-2-butanol, polyols such as 1,4-butanediol, neopentylglycol, trimethylopropane, pentaerythritol monopropylene glycol, ethylene glycol and where applicable cyclic alcohols such as cyclohexanol or alcohols carded by an aromatic group such as the phenol-propanols.

These oxidizing agents, preferably without water, are introduced into the catalyst preparation medium in a neutral or hydrogen gas atmosphere, identical to that described in step (b).

The quantity of oxidizing agent O used is generally greater than the quantity necessary for total oxidation of the reducing compound R which has not reacted during step (b) of reduction of the metal compound.

A quantity of the oxidizing additive O is added such that the ratio between the number of oxidizing functions of the compound O and the number of reducing functions contained in the reducing agent R which have not acted in the reduction of the metal A compound (calculated number) is between 1 and 20 and preferably between 1.5 and 10.

This neutralization is carded out in a neutral or reducing gas atmosphere, wherein:

the partial pressure of hydrogen is between 0 and 200 bar, preferably between 0.01 and 50 bar and most advantageously between 0.1 and 10 bar, the temperature is between −20° C. and 200° C. and preferably between 0° and 150° C.

As after steps (b) and (c), a ripening step is carried out according to the conditions of temperature and partial hydrogen pressures defined hereinabove; the ripening time is between 0.1 minute and 100 hours, preferably between 1 minute and 75 hours and most advantageously between 10 minutes and 50 hours.

The step (d) of neutralizing, the residual reducing functions of the reducing agent R still present in the catalytic solution after reduction of the metal A by at least one oxidizing agent O generally results in a product soluble in the hydrocarbonic medium, even when saturated with water. If this step (d) of preparation of the catalyst is not carded out, the water present in the batch can have a double de-activating effect:

the excess reducer is suddenly destroyed by the water, generally together with the formation of products which are hardly soluble or insoluble in the medium; the particles (for example of aluminium hydroxide where the reducer is triethylaluminium) tend to trap part of the active catalyst, and/or the reaction of water with the metal more or less reduced by and coordinated with the reducer (A-R' or R' can for example be an Al-Et radical if the reducer is triethylaluminium) resulting in a less active component.

The most important characteristic of the method according to the invention is in the last step of preparation which consists of the removal of the reducing functions of the reducing agent R by means of an oxidizing agent O while retaining perfect solubility and constant activity of the catalyst prepared in this manner in the moist reaction medium. Without this neutralizing, the residual reducing functions are progressively oxidized by the water present in the batch to be hydrogenated with, as a consequence, precipitation of this hydrolyzed catalyst fraction rendered inactive, and formation of agglomerates which more or less trap a part of the active catalyst, thus lowering the catalytic performance of the whole.

The moist reaction medium (or liquid phase) is defined as including a quantity of water equal to or greater than the maximum quantity which can be present in dissolved form and perfectly homogeneous in said organic medium.

The object of the invention is also a method of selective or total hydrogenation in liquid phase and homogeneous phase, of unsaturated mono-olefinic or polyolefinic, acetylinic, and aromatic compounds, and of saturated or unsaturated functional compounds with a catalyst prepared as described hereinabove.

Advantageously, said catalyst prepared in this manner allows hydrogenation to be carried out with a liquid phase including quantities of water equal to or less than the maximum quantity which can be present in dissolved form and perfectly homogeneous in said organic medium. In other words, the hydrogenation method can be carried out in the presence of discrete water in the reaction medium.

The hydrogenation method is carded out at a temperature of between 0° and 400° C. and advantageously between 20° and 300° C. and at a partial hydrogen pressure of 0.01 and 20 MPa, and preferably between 0.1 and 5 MPa.

The following examples illustrate the invention. Examples 2 to 6 describe the preparation of catalysts according to the prior art. They am tested by way of comparison in example 12.

EXAMPLES

Example 1 (Invention)

0.1 moles of triethylaluminium in solution in 1 l of perfectly dry and de-aerated benzene is placed into a perfectly dry glass flask purged with argon.

0.1 moles of nickel octoate is introduced into a second flask, which is also dry, and then purging with argon takes place. 1 l of perfectly dry and de-aerated benzene is then added.

After dissolving, 100 cm$^3$ of the nickel octoate solution is introduced into a third perfectly dry flask purged with argon, equipped with a magnetic bar stirrer and placed in a water bath kept at approximately 25° C. Then 80 cm$^3$ of the triethylaluminium solution is progressively injected in such a manner that the duration of the injection is at least 10 minutes and that the temperature of the medium does not exceed 50° C.; the flask is kept lightly swept with hydrogen at atmospheric pressure.

After introduction of the whole of the reducer, the temperature of the bath is increased progressively up to 50° C., then agitation takes place for one hour.

Having completed this ripening step, 1 mmole per minute of dry tertiary butyl alcohol is injected for 8 minutes, still with the light sweep of hydrogen at atmospheric pressure and at the temperature of 50° C.

Having completed the injection of alcohol, the product is agitated in a hydrogen atmosphere, and at 60° C. for 2 hours before the finished catalyst is used.

Example 2 (Comparison)

The preparation described above is repeated, with the exception of the step of neutralizing the excess reducer AlE3 with t-butanol.

Example 3 (For Comparison with Example 4, U.S. Pat. No. 4,357,478)

A solution of triethylaluminium is added to a solution of 0.1 mole of nickel decanoate and 0.02 moles of decanoic acid in 17 cm$^3$ of benzene, such that the Ni/Al ratio is equal to 3.

Example 4 (For Comparison with Example 1, U.S. Pat. Nos. 4,980,331 and 5,030,779)

0.05 moles of ethyl 2-nickel hexanoate in solution in cyctohexane is introduced into a glass flask at 25° C., then methylalumoxane such that the Al/Ni ratio is equal to 3. After 30 minutes of agitation, triethylaluminium with a Ni/Al ratio equal to one is injected. The catalyst is used 30 minutes after preparation thereof.

Example 5 (Comparison with Example 2, U.S. Pat. No. 3,541,064)

0.06 moles of nickel naphthanate is mixed in solution in toluene with 0.24 moles of butyllithium, The catalyst is used after 5 minutes of agitation at 30° C.

Example 6

The preparation described in example 3 is repeated, with the exception that the equivalent of 0.2 moles of cyclohexanol is injected into the product obtained and that ripening for a period of 2 hours is carried out at 50° C.

Example 7

The preparation described in example 4 is repeated, with the exception that 0.4 moles of isobutanol Is injected into the product obtained after the 30 minutes of contact following the injection of triethylaluminium and ripening for a period of 8 hours is carried out at ambient temperature.

Example 8

The preparation described in example 5 is repeated, with the exception that the equivalent of 0.5 moles of isopropanol is injected into the product obtained at 20° C. and that the temperature of the mixture is then increased to 60° C. for 1 hour.

Example 9

A catalyst is prepared according to the method described in example 1, the only difference being that after mixing the solution of nickel and alkylaluminium, the solvent being cyclopentane and the ripening period being carried out at 10° C., 0.2 moles of pyridine is introduced, which is kept agitated at ambient temperature before injecting neutralizing alcohol, still at a temperature of 10° C.

Example 10 (Comparative)

The preparation as described in example 9 is repeated with the exception of the phase of neutralizing with alcohol.

Example 11

A catalyst is prepared according to the method described in example 1, with the only difference being that all of the preparation is carried out in argon with cyclododecatriene as the solvent, and that the metal A compound is cobalt naphthanate. The neutralising step is carried out with cyclododecanol at a temperature of 120° C. with an agitation time of 4 hours. The total hydrogenation of 1 litre of cyclododecatriene into cyclododecane is total after one hour of reaction in 30 bars of hydrogen and at 180° C.

Example 12

A 0.001 molar nickel octoate solution in cyclohexane and a 0.001 molar triethylaluminium solution, also in cyclohexane, is injected at ambient temperature under pressure by means of 2 pumps into a pipeline connected to a benzene hydrogenation reactor which acts as a reactor for preparation of the catalyst, such that the Al(Et)$_3$/octoate molar ratio is 1.5. In this same pipeline, but at a distance of 2 m from the place where the metal-reducer mixture takes place, t-butanol is injected by means of a third pump such that the alcohol/Al(Et)$_3$ ratio is 2.

The catalytic mixture is carried towards the hydrogenation reactor which is several meters away. The perfectly agitated reactor is continuously supplied with benzene including approximately 400 ppm of dissolved water and with hydrogen at 20 bar pressure. This benzene, hydrogenated at 200° C. in cyclohexane, is continuously removed in vapor phase. The concentration of catalyst continuously injected into the reactor at the same time as the batch of benzene is equivalent to 20 ppm of nickel so that the amount of hydrogenation of the aromatic hydrocarbon is greater than 98%.

Example 13

The test described hereinabove is repeated with the same temperature, pressure and spatial speed conditions for the reactants, as well as with the same batch of benzene including 400 ppm of water, but the injection of terbutylic alcohol, allowing neutralizing of the excess of triethylaluminium reducer, is not carried out. It has been observed that to obtain the same yield of benzene hydrogenation in cyclohexane it is imperative that the nickel concentration in the benzene batch entering the reactor is at least 50 ppm.

Example 14

The catalysts from example 1 to 10 are batch tested in selective or total hydrogenation reactions of unsaturated hydrocarbonic compounds in the presence or the absence of discrete water (lower limit of saturation); the test results are arranged in the table below. The operating conditions are identical for the same reactant, whether the medium contains water or not.

The operating conditions:

| Examples 1 and 2 | T = 200° C. | P = 2 MPa |
| Examples 3 and 6 | T = 200° C. | P = 1.5 MPa |
| Examples 4 and 7 | T = 200° C. | P = 3 MPa |
| Examples 5 and 8 | T = 180° C. | P = 1 MPa |
| Examples 9 and 10 | T = 25° C. | P = 1.5 MPa |

| Example | | Conc. mxt. m.atom /2 | Reactant | H$_2$O + with − without | Conversion % | Selectivity % |
|---|---|---|---|---|---|---|
| 1 | inv. | 5 | benzene | — | 98 | 99.8 |
| 2 | comp. | 5 | " | 800 ppm | 85 | 99.7 (cyclohexane) |
| 3 | comp. | 7 | toluene | + | 95 | 99.4 |
| 6 | inv. | 7 | " | + | 83 | 99.8 (m. cyclohexane) |
| 4 | comp. | 8 | naphthalene | 300 ppm | 70 | 95 (tetraline) |
| 7 | inv. | 8 | " | 300 ppm | 95 | 98 (tetraline) |
| 5 | comp. | 12.0 | cyclododecatriene | + | 85 | 99.9 (cyclododecane) |
| 8 | inv. | 8.5 | " | + | 92 | 99.9 |
| 9 | inv. | 2.0 | cyclopendiene | − | 99.9 | 96.5 (cyclopentene) |
|  |  | 2.0 | " | + | 99.6 | 98.5 |
| 10 | inv. | 3.0 | " | − | 99.9 | 96 |
|  |  | 4.0 | " | + | 99.7 | 95.5 |

The above results illustrate the improvement brought about by the neutralizing of the excess reducer in the hydrogenation reaction of unsaturated compounds carried out in the presence of discrete water, which have good activity as well as selectivity.

We claim:

1. In a method of preparation of a catalyst in a homogeneous phase, soluble in an organic medium, said method comprising:

(a) reacting a solution of at least one compound of at least one metal A in at least one organic solvent S with at least one compound R of at least one metal B, in at least one organic solvent S', said solvents S and S' solubilizing said compounds and being essentially free of oxidizing agents, said compound R capable of reducing said compound of metal A, the improvement comprising subsequent to (a), and prior to use of the catalyst, (b) neutralizing residual reducing capacity of the reducing compound R for the compound of metal A with at least one oxidizing agent O.

2. A method according to claim 1, wherein a selectivity agent P is added to the solution of the metal compound prior to contacting with the reducing compound.

3. A method according to claim 1, further comprising (c), adding a selectivity agent P to the product resulting from (b).

4. A method according to claim 1, carried out at between −20° and 200° C.

5. A method according to claim 1, further comprising, subsequent to (b), a ripening step taking place at between −20° and 200° C. and for between 0.1 min. and 100 hrs.

6. A method according to claim 1, wherein the metal A is at least one metal of groups Ib, IIb, Vb, VIb, VIIb or VIII of the periodic classification.

7. A method according to claim 1, wherein the metal A is at least one metal of groups Ib, VIb, VIIb or VIII.

8. A method according to claim 1, wherein the metal A is iron, cobalt, nickel, copper chrome, molybdenum, manganese or zinc.

9. A method according to claim 1, wherein the metal A compounds are halides, sulphides, acetylacetonates or carboxylates of organic acids with 2 to 25 carbon atoms.

10. A method according to claim 1, wherein the metal A compounds are acetates, octoates, decanoates, naphthanates, stearates, palmitates, oleates or benzoates.

11. A method according to claim 1, wherein the reducing compound R is an organometallic derivative of at least one metal B which is lithium, sodium or aluminum.

12. A method according to claim 1, wherein the reducing compound R is triethylaluminum, triisobutylaluminum, chlorodiethylaluminum, diethyltertbutoxyaluminum, diethoxyethylaluminum, diisobutylaluminum hydride, mixed lithium and aluminum hydride, mixed sodium and aluminum hydride, mixed sodium and a boron hydride, butyllithium, sodium ethylate or a derivative of, any of the above produced by substitution with a hydrocarbonic or alkoxy radical.

13. A method according to claim 1, wherein the solvents S and S' are saturated or unsaturated hydrocarbons, monoaromatic compounds, polyaromatic compounds, saturated or unsaturated alkylbenzenes, saturated or unsaturated monocyclic compounds, oxides or ethers.

14. A method according to claim 1, wherein the concentration of the compound of metal A in the solution S is 0.01 to 10 moles per liter.

15. A method according to claim 1, wherein the concentration of the compound of metal B in the solution S' is 0.01 to 10 moles per liter.

16. A method according to claim 1, wherein the reduction of the metal A compound by compound R is carried out with a ratio between the reducing capacity of compound R and the oxidizing capacity of the compound of metal A of 0.1 to 20.

17. A method according to claim 1, wherein the reduction of the metal A compound by the compound R is carried out with a ratio of reducing capacity of the reducing agent R to the oxidizing capacity of the compound of metal A of 0.5 to 10.

18. A method according to claim 2, wherein the selectivity agent P is a compound of at least one metal of groups IA, IIA or IIB of the periodic classification, yttrium, titanium, zirconium, gallium, germanium, arsenic, tin, lead, phosphorous or antimony.

19. A method according to claim 2, wherein the selectivity agent P is an organic compound which is a phosphine, amine, sulphur-containing compound or nitrogen-containing compound.

20. A method according to claim 2, wherein the atomic or molar ratio of the selectivity agent P and the metal A compound is 0.001 to 10.

21. A method according to claim 1, wherein the oxidizing agent O is a primary or secondary long-chain aliphatic alcohol with a number of carbon atoms at least equal to 6, a linear or branched tertiary alcohol, a cyclic alcohol, an alcohol attached to an aromatic group or a polyol.

22. A method according to claim 1, wherein the quantity of oxidizing agent O added is such that the ratio of the oxidizing capacity of the O compound to residual reducing capacity of compound R is 1 to 20.

23. A method according to claim 5, wherein (a), (b) and the ripening step are carried out in an inert gas or reducing gas atmosphere.

24. A method according to claim 23, wherein the reducing gas is hydrogen, and the partial pressure of hydrogen is between 0 and 200 bar.

25. A method for selective or total hydrogenation in the liquid phase and in a homogeneous phase, of unsaturated mono-olefinic or polyolefinic, acetylinic, or aromatic compounds, and of saturated or unsaturated functional compounds, comprising contacting said compounds under effective conditions with a catalyst prepared according to claim 1.

26. A method of hydrogenation according to claim 25 in which the liquid and homogeneous phases include quantities of water equal to or less than the maximum quantity which can be present in dissolved form and perfectly homogeneous in said organic medium.

27. A method according to claim 25, wherein the liquid or homogenous phases contain water.

28. A method according to claim 25, wherein the compound subjected to hydrogenation is not a phenol.

29. A method of preparation of a catalyst in a homogeneous phase, soluble in an organic medium, said method comprising:

(a) reacting a solution of at least one compound of at least one metal A from group Ib, IIb, Vb, VIIb or VIII in at least one organic solvent S which is essentially free of oxidizing agents and is a saturated or unsaturated hydrocarbon, a monoaromatic compound, a polyaromatic compound, a saturated or unsaturated alkylbenzene, a saturated or unsaturated monocyclic compound, oxide or ether, with at least one compound R of at least one metal B, which is an organometallic derivative of lithium, sodium or aluminum, in at least one organic solvent S' which is essentially free of oxidizing agents and is independently selected from those given for S, said solvents S and S' solubilizing said compounds, said compound R capable of reducing said compound of metal A, (b) subsequent to (a), and prior to use of the catalyst, neutralizing all residual reducing capacity of the reducing compound R to the compound of metal A with at least one oxidizing agent O which is a primary or secondary long-chain aliphatic alcohol with at least 6 carbon atoms, a linear or branched tertiary alcohol, a cyclic alcohol, an aromatic alcohol or a polyol.

30. In a method of preparation of a catalyst in a homogeneous phase, soluble in an organic medium, said method comprising:

(a) reacting a solution of at least one compound of at least one metal A in at least one organic solvent S with at least one compound R of at least one metal B, in at least one organic solvent S', said solvents S and S' solubilizing said compounds and being essentially free of oxidizing agents, said compound R capable of reducing said compound of metal A, the improvement comprising subsequent to (a), and prior to use of the catalyst, (b) neutralizing residual reducing capacity of the reducing compound R to the compound of metal A with at least one oxidizing agent O, which is not a phenol.

31. A process according to claim 30, wherein all residual reducing capacity of R is neutralized.

32. A method according to claim 1, wherein the solvents S and S' are benzene, toluene, xylene, naphthalene, cyclohexane, cyclohexene, decahydronaphthalene, 1,2,3,4-tetrahydronaphthalene, tetrahydrofuran, or methylic ethers of diethylene glycol.

33. A method according to claim 1, wherein solvents S and S' are free of traces of oxidizing agents.

34. A method according to claim 29, wherein solvents S and S' are free of traces of oxidizing agents.

35. A method according to claim 30, wherein solvents S and S' are free of traces of oxidizing agents.

* * * * *